United States Patent [19]

Leser

[11] Patent Number: 4,492,477
[45] Date of Patent: Jan. 8, 1985

[54] PROCESS AND APPARATUS FOR THE DETECTION OF FLAWS IN TRANSPARENT SHEETS OF GLASS

[75] Inventor: Jacques F. Leser, Montpellier, France

[73] Assignee: CEM Cie Electro-Mecanique, Paris, France

[21] Appl. No.: 349,621

[22] Filed: Feb. 17, 1982

[30] Foreign Application Priority Data

Feb. 25, 1981 [FR] France ............... 81 04139

[51] Int. Cl.³ ........................... G01N 21/89
[52] U.S. Cl. ........................ 356/430; 250/572; 356/239
[58] Field of Search ............ 356/237, 239, 430, 431; 250/562, 563, 572; 358/106

[56] References Cited

U.S. PATENT DOCUMENTS

| | | | |
|---|---|---|---|
| 2,803,755 | 8/1957 | Millford | 356/431 X |
| 3,445,672 | 5/1969 | Marks | 356/237 |
| 3,877,821 | 4/1975 | Price et al. | 356/237 |
| 4,038,554 | 7/1977 | Craig | 250/572 |
| 4,223,346 | 9/1980 | Neiheisel et al. | 356/430 X |
| 4,277,178 | 7/1981 | Cushing et al. | 356/431 |
| 4,308,959 | 1/1982 | Hoover et al. | 358/106 X |

Primary Examiner—Vincent P. McGraw
Attorney, Agent, or Firm—Burns, Doane, Swecker & Mathis

[57] ABSTRACT

The present invention relates to a method for checking flat transparent surfaces permitting the discrimination between the flaw in the matter and dirt which has been deposited on the surface but does not affect the flatness or the transparency of the sheet. The apparatus includes a photosensitive captor located above the sheet to be checked. The captor is arranged at the limits of a fuzzy real image which an optical system gives in the plane of this captor of a light source located below the sheet. In this way, a flaw causes the excitation of the captor at a level higher than the normal light threshold of the fuzzy image because of refraction caused by the flaw in the matter. In contrast, the presence of dirt will cause, through occultation, an excitation lower than the normal light threshold thereby enabling differentiation between the flaw and the dirt. The apparatus further includes an electronic assembly for analyzing the signals provided by the captor for driving a device for marking the surface bearing a flaw at the exact spot where the flaw is located. The present invention may be used for checking glass sheets during their manufacturing in continuous or cut out glass sheets for example.

14 Claims, 20 Drawing Figures

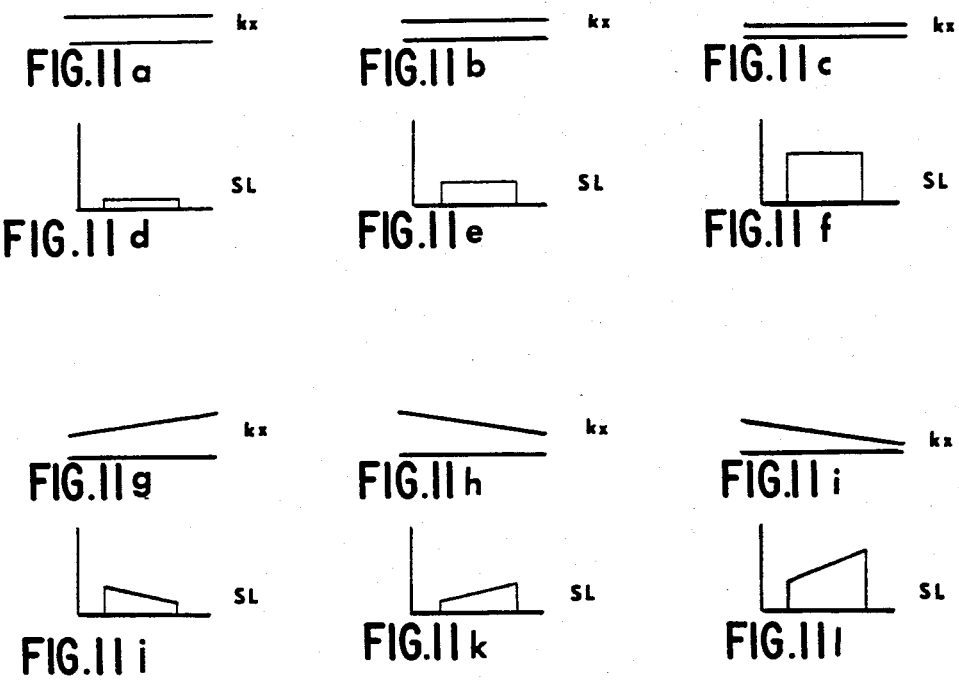
FIG.11a FIG.11b FIG.11c
FIG.11d FIG.11e FIG.11f
FIG.11g FIG.11h FIG.11i
FIG.11j FIG.11k FIG.11l
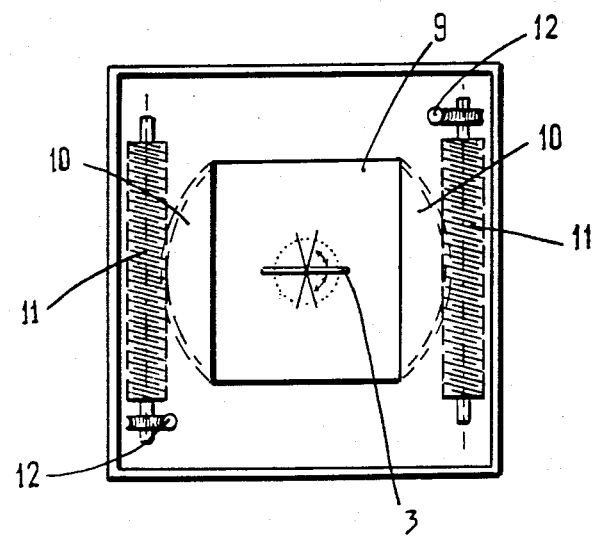
FIG.12

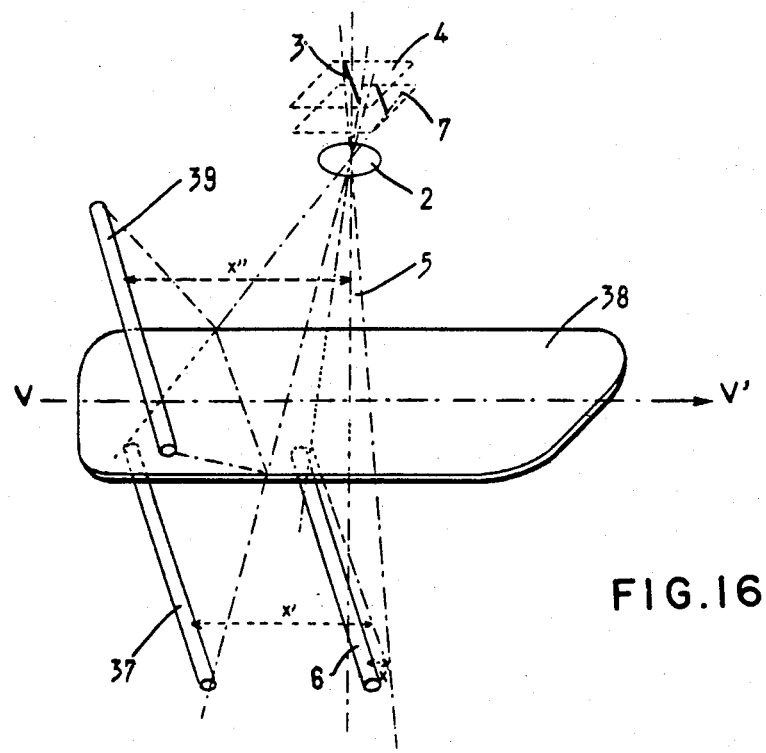
FIG.16
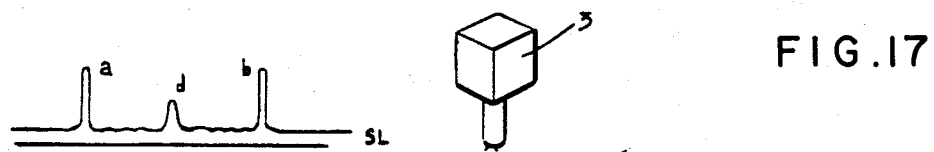
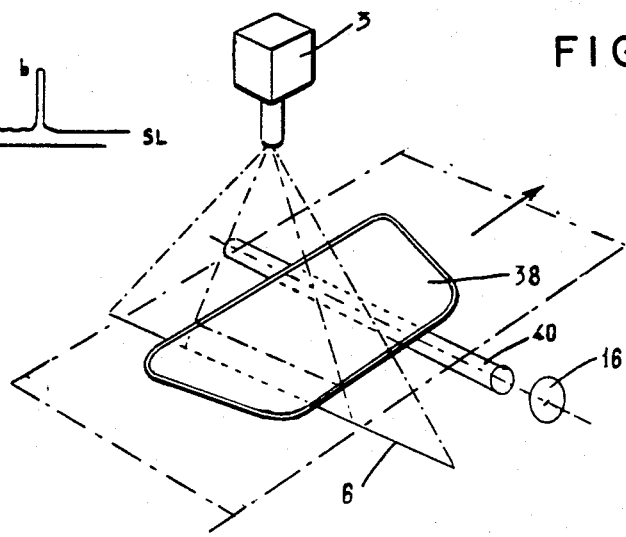
FIG.17
FIG.18

PROCESS AND APPARATUS FOR THE DETECTION OF FLAWS IN TRANSPARENT SHEETS OF GLASS

BACKGROUND AND SUMMARY OF THE PRESENT INVENTION

The present invention relates to a process for the inspection of transparent sheets passing by continuously or in separate sections, in order to detect flaws, even minimal flaws, which the sheet might include. Further, the process does not detect foreign bodies or soil that may be present on the sheet surface which bodies or soil to not affect the planar nature of the sheet and may be eliminated by a simple washing. The present invention also relates to an apparatus for applying the process.

Processes are known, together with devices for their application, that are capable under certain conditions of detecting flaws present on the surface of a flexible film, such as a photographic film.

The object in these known processes is to detect all of the flaws of the support or of an emulsion deposited on the film, together with all of the soil or foreign bodies present on the surface. It is very difficult to eliminate the soil from the film by simple washing since the emulsion cannot tolerate such a washing. In other words, anything that may alter the purity of the surface of the film inspected must be considered a flaw.

The situation is entirely different in the case of the inspection of glass during its manufacture by the process, for example, of flotation on a bath of molten tin, designated the "float glass" process. In this case, only the flaws of the materials itself: bubbles, drops, inclusions, projections of tin, for example, are to be detected, because they affect the flatness and the transparency of the glass. On the other hand, it is unnecessary to detect simple dirt of any nature found deposited on the surface, because simple washing is sufficient to eliminate the dirt. The detection of dirt as a flaw may lead to the rejection of a perfectly usable portion of the glass.

It is therefore desirable to effect in this case a finely selective method of detection, capable of substantially perfect discrimination between flaws of the material and surface soil that may be carried by the material.

Furthermore, the known processes generally use a laser beam made to scan the surface of the material in a cyclic manner, and reflect from an assembly of rotating or oscillating mirrors.

Such processes thus include mechanical elements which are a source of imperfection and make difficult the perfect synchronization between optical scanning by the laser beam and the velocity of the passage of the glass surface particularly when it is necessary to modify the glass surface velocity. Accordingly, such a process may impose the condition of a constant velocity, which represents a restriction that may become a disadvantage.

Finally, the cost of the use of devices for the application of such processes is high, due to the high expense of the source of the laser beam. Also, the laser beam source in a glass manufacturing plant is subject to a high risk of deterioration.

These disadvantages apply among others to a device of the type described in French Patent No. 2,238,930 and to the earlier patents cited in this patent.

Furthermore, most of the known processes require frequent standardization as the result of the variations that may occur either in the intensity of the luminous source or in the reflectivity of the rotating or oscillating scanning mirrors which may rapidly become charged with impurities. Standardization may also be required for even a simple change in the thickness of the glass from one product to another or in the refringence or the tint of the glass. Such standardization is actually necessary practically for each scanning resulting in an increased complexity of the automatic control system and thus in an increase in cost.

Finally, concerning devices which operate by reflection from the sheet of glass to be inspected, it has been found that they are not suitable for the inspection of continuous sheets of glass. In actual fact, the length of the band in this case and the stresses acting upon the sheets are such that the surface is almost constantly exposed to vibrations, which cause aberrations in the reflected beam, if such devices are used.

According to certain other processes, the radiation used consists of infrared rays. Such a process and device are described in French Patent Nos. 1,435,210 and 2,099,921. These arrangements do not permit a selection among flaws of the material and simple soil that adheres to the material surface. Detection of soil may be satisfactory or even necessary for the object of the two patents which relate to the control of the quality of photographic strips but such detection is not satisfactory for the purpose of the present invention, as this would result in the automatic rejection of portions of the glass that are simply soiled but perfectly usable after a simple washing.

It is to be noted further that in each of these patents the source of light is located in the geometric plane which also contains the flaw to be detected, the optical axis of the focussing device and the detector element.

The deviation of the incident luminous rays, either by reflection or by refraction, due to the deformation of the surface of the material produced by a flaw which deforms the material slightly causes in each of these cases a reduction in the quantity of light normally received by the detector element. In other words, the deviation diverts the light rays from the optical axis of the captor upon which the liminous source is located. The image of a flaw is thus always a more or less dark spot appearing on a peripheral bright field. This process is designated the "bright field" projection process hereinafter.

It is seen therefore that any foreign body located on the surface of the glass will be detected in the same manner as a flaw of the material itself.

While nonselective detection of this type is desirable in the case of the inspection of emulsified photographic film, the situation is different in the inspection of glass wherein only material flaws are to be considered, regardless of their nature. These flaws include even partial inclusions of foreign bodies, but exclude any soiling due to the presence of the same foreign bodies, when they are simply positioned on the surface of the glass without deforming the surface since such foreign bodies are capable of elimination by a simple washing process.

It is further noted that the contrast created by a dark image on a bright background is difficult to detect. Accordingly, such an arrangement limits the fineness of such detections.

It is therefore an object of the present invention to attain the result necessary in the inspection of sheets of glass in the course of their manufacture by eliminating the aforementioned disadvantages inherent in each of the known processes when applied to the specific case under investigation. The process desired should be perfectly selective and should allow the elimination of only those portions of the glass being produced which portions exhibit real flaws of the material, regardless of their nature or dimensions, even the smallest flaws, without the indication of superficial soil which does not mark the surface of the glass.

In order to accomplish this object according to the principles of the present invention, the deviation of the light rays caused by the presence of a flaw affecting the surface of the glass and, as indicated hereinabove, diminishing the intensity of the image yielded by the optics of the source of light located on its axis, is utilized here, in contrast to the known processes, to cause an increase in the light with respect to the general image produced by the same source. In this way, it is possible, as may be seen and in contrast to the other processes, to differentiate flaws of the material from simple soil deposited on that surface which soil still causes a reduction in the luminous intensity by simple occultation according to the present invention.

It has been found in fact that any flaw of the material, whether it consists of bubbles, blow holes, drops, or even partial inclusions, causes flatness defects on the glass surface. In other words, a more or less severe deformation of the surface is found at this level, which, however, is always present. The object of the present invention is thus to utilize the deviation of the luminous rays caused by a surface flaw of the glass to render the image even more luminous than the general image of the source of light. This deviation being obtained by the effect of refraction in the mass of glass deformed. This effect is not produced by simple soiling.

In the present process of discriminating against flaws due to dirt, the use of the deviation of light rays by diffraction, commonly used in the so-called "dark field" process, has been eliminated. The "dark field" process consists of darkening the light in the center of the optics, so that no rays are penetrating directly into said optics. The object to be observed is illuminated solely in an oblique manner by intense peripheral rays. The rays are diffracted by the object and are the only ones penetrating into the optics, thereby forming a clear image of the object on a dark background.

It is obvious in this case, that the flaws of the surface will produce a luminous zone on a dark background, which zone because of this fact may be detected more readily than the previously described inverse image, by virtue of its better contrast. However, independently of the fact that such a process requires an intense source of light, it has been found that the images of all opaque foreign bodies, which generally constitute the soil deposited on the surface of the glass, also appear haloed by light on the black background. This detection of foreign bodies causes the actuation of any photosensitive device in the same manner as a surface defect. Consequently, selectivity of the process is eliminated.

For this reason, according to the present invention, it is not diffraction that is applied to the surface defects of the glass, but refraction. The defects are able to produce refraction in the same manner as a prism or a lens, as they may be considered generally to be aspherical, warped lenses of a more or less pronounced configuration, and having a more or less oblique optical axis.

The process that is the object of the present invention thus consists, according to a preferred embodiment, of utilizing the deviation of the incident luminous beam due to the deformation of the surface of the material produced by a flaw, to increase the quantity of light normally received by the captor toward the optical axis from which the deviation is randomly projecting luminous rays that normally are not perceived. Such an increase in light could not be caused in any case by simple dirt. To accomplish this result, a point source of light with a low intensity is used. The light is placed, in contrast to the known processes, outside but in close proximity to the optical plane also containing the optical axis of a focussing device at the end of which is located the photosensitive detection element.

In this manner, a condition that may be called a "mixed field" is created. The "mixed field" may be understood by recalling that the "bright field" is produced when the observer, or the photosensitive element, and the luminous source are on the same optical axis, which also contains the flaw to be observed. The flaw appears as a dark spot on a bright background. Since the flaw has refracted the light outside the optical field, or darkened the light if an opaque foreign body is involved. The result appears in an identical fashion as a dark spot on a bright background, which spot is difficult to observe and nonselective. In the "dark field", which also assumes the alignment on the optical axis of the observer, the source of light and the object is obtained by illuminating the object by an intense peripheral beam which is diffracted toward the optical axis, causing a luminous image of the object to appear on the dark background. This luminous image is not any more selective than the dark spot, even though it has more contrast.

The "mixed field" thus has the effect of rendering the image of a surface flaw of a sheet of glass in the form of a bright image on a dark background, essentially as in the case of the dark field. However, the bright image is no longer an effect of diffraction but rather one of refraction, which has the essential and novel consequence that a selection between flaws of the material and dirt is assured, as the dirt cannot create the refractive effect desired. Accordingly, the "mixed field" is different from that of the dark field. The "mixed field" also has the further advantage of providing a substantial contrast in the detection of flaws which contrast comprises a bright image on a dark background, different from the result of the bright field.

This result is obtained according to the process of the present invention by distancing the low intensity point source of light away from the optical axis of the detection system by a small value but one that is sufficient so that the light captor is at the limits of the image produced in its plane of the source of light by the optical system. With this arrangement, in the absence of a deformation of the surface of the glass, the observer or the photosensitive element substituted for the observer can receive only the limiting fringe of the image of the luminous source. This arrangement assures a generally low level of illumination and is called being at the limits of the "bright field".

It may be understood then that the slightest deviation of the light rays caused by refraction due to an internal or superficial deformation of the glass will cause the rays penetration into the optical system. This refraction produces in the plane of the captor an image with a higher luminous intensity, defined in a perfectly contrasted manner on the dark fringe of the image of the light source which remains unchanged and at the outside of which the luminous image of the flaw appears.

It will also be understood that only flaws of the glass are capable of creating the refraction necessary to form the luminous image. Dirt appears only as a deeper darkening of the mixed field, which makes it possible to distinguish it from the flaws investigated. This differentiation of dirt and flaws is facilitated even more by the fact that the light source is of low intensity, thereby eliminating the possibility of diffraction at the level of the periphery of soil.

The process according to the present invention thus makes it possible to obtain the selectivity desired while providing a fineness of the detection of flaws limited only by the sensitivity of the photosensitive detector elements.

The device for the application of the process of the present invention thus essentially comprises a filiform, i.e., thread-like source of light adapted to cover the entire width of the band to be inspected and placed under the sheet of glass passing above the light source. The source of light comprises one or more fluorescent tubes, installed for example end to end depending on the width of the sheet of glass to be inspected, and placed transversely with respect to the direction of passage of the glass. In order to illuminate its entire width, a narrow, longitudinal slit is provided in the cox containing the sources of light. An optical focussing device is placed over the glass to be inspected. The focussing device is located in relation to the light source and the sheet of glass such that each of them is outside their respective foci, to form a real, clear image of the surface of the glass and of all that it supports in the plane. An assembly of juxtaposed photodiodes is placed for exploring the entirety of the image formed in a continuous manner.

And, as mentioned hereinabove, the source of light is removed from the optical axis of the system by a value just sufficient so that the grid of photodiodes is located on the extreme fringe of the light source image and parallel to the light source. In this manner, in the absence of any deformation of the surface of the glass, the photodiodes are impacted only slightly, in a uniform manner, in keeping with a relatively low threshold, designated the "light threshold". In contrast, upon the appearance of any deformation of the surface of the glass, even when very small, the light rays are sufficiently deviated by refraction so that some of the light rays will traverse the optical system, thereby forming a luminous image which impacts certain of the photodiodes, stressing them at a very precise point until a higher threshold, designated the "flaw threshold" is attained. Reaching the "flaw threshold" causes a signal of known coordinates to be emitted which will be processed by an electronic assembly actuating a system for issuing instructions. The instructions are interpreted to eliminate or to simply mark the part of the glass affected by the defect.

It will be understood further that an impurity that does not deform the surface of the glass and therefore does not constitute a permanent flaw, will produce in such a system an even more substantial weakening of the luminous intensity of the image received by the captor. The image at this point passes under the standard light threshold, so that the signal emitted in this case by any one of the photodiodes will obviously be different from that generated by a flaw of the material.

BRIEF DESCRIPTION OF THE DRAWINGS

The drawings attached hereto, presented as examples only, illustrate a preferred embodiment of a device for the application of a process according to the present invention in the case of the inspection of a continuous sheet of glass during manufacture and in the case wherein sheets of glass are travelling in a continuous or noncontinuous fashion.

FIG. 11 is schematic representations of integrated signals emitted by the captor as a function of the distance of the light source in relation to the optical axis of the captor and the parallel location of the light source with respect to the captor itself in the case of a linear source of light;

FIG. 12 is a schematic view of a device for ensuring that the distance of the light source to the optical axis of the captor remains constant and that the linear source of light remains parallel in relation to the captor;

FIG. 16 is a schematic view of the general layout of the device for the application of the process according to the present invention in the specific case of the inspection of precut sheets of glass, such as sheets of glass intended for the production of laminated or tempered windshields, for example; and FIG. 17 is a schematic view of the device for the application of the process of the invention in the case illustrated in FIG. 16.

DETAILED DESCRIPTION OF THE PREFERRED EMBODIMENT

Figures 1, 2A, 2B:
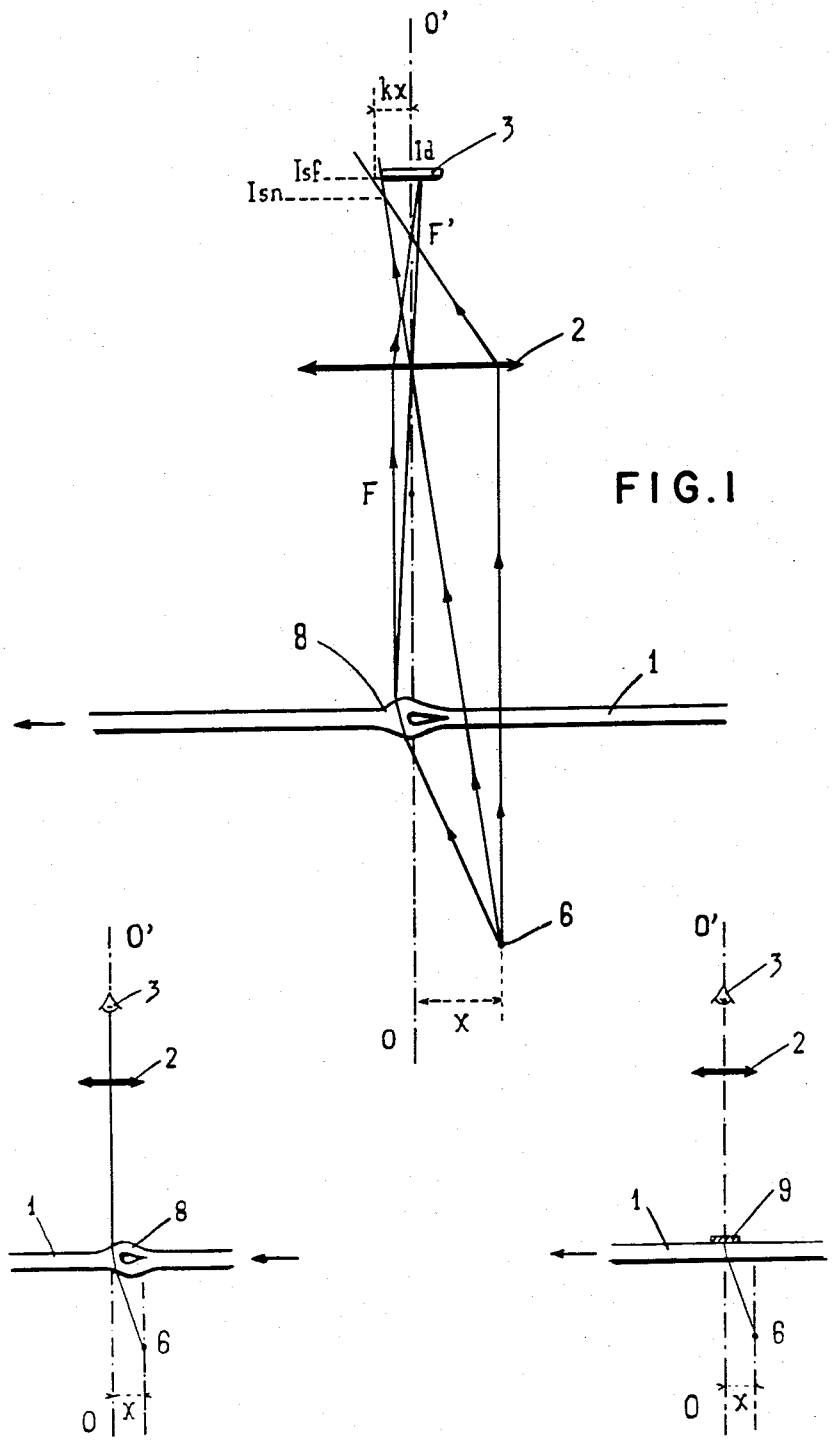
FIG. 1 is a diagram demonstrating the principle of the process according to the present invention.
FIGS. 2A and 2B are simplified optical diagrams of the same principle illustrating the case of a flaw and of dirt.

With reference to FIG. 1, a convergent optical system or objective is located between a photosenstitive captor 3 and a sheet of glass 1 that is to be inspected. An axis 00', which contains the captor 3, is orthogonal to the plane of the sheet of glass 1, which is passing continuously in a plane beyond the focus (F) of the objective 2, in a manner so that the real image (Id) produced by the objective 2 of the sheet of glass 1 and flaws or impurities the sheet contains is formed exactly in the plane of the captor 3. The depth of the field of the objective 2 is sufficient for the images of each of the faces of the sheet of glass will be clear simultaneously in the same plane, regardless of the sheet thickness.

A low intensity point source of light 6 is located under the plane of the sheet of glass 1. It is seen that the captor 3 consequently receives in its plane only a blurred image (Isf) of the source of light 6. The clear image of the light source is formed in the plane (Isn) distinct from that of the captor 3.

Thus, if the light source 6 is located on the optical axis 00', which in itself would not permit distinguishing a flaw from soil, both would be translated by a weakening in their image plane of the luminous intensity, one by the deviation of the luminous rays, the other by occulation. Contrast would remain weak, not allowing for great precision.

Accordingly, by the present invention, the source of light 6 is displaced from the optical axis 00' to a distance (x), so that the blurred image produced by the objective 2 of the source is distant from the optical axis by a value of (kx). (k) is the ratio of reduction of the objective 2 and the value (kx) corresponds to the half width of the captor 3. In this way, captor 3 will be externally tangent to the blurred image, formed in captor plane, of the source 6. The captor thus receives only a minimum amount of light from the source 6. In this manner, in the absence of a flaw the captor 3 is excited very weakly only by the extreme fringe of the blurred image of the source 6 with a value that is constant in time.

It should be understood that a very slight deviation of the beam of light caused by the presence of a flaw 8 of the surface of the glass is sufficient to deflect at least part of the light previously tangent to the captor 3 by refraction by the flaw. This deflection forms an actual bright image of the flaw in the captor 3, which image appears in high contrast surrounded by a darker zone.

FIG. 2A is a diagram similar to FIG. 1 in a simplified manner corresponding to the presence of a flaw 8 on the surface of the glass 1.

In contrast, FIG. 2B is an illustration of a foreign body 9 or a spot located on the surface of the glass (lower or upper surface) which spot does not cause any deformation of the material (since the spot is not included even partially in the mass of the glass). Consequently, the foreign body 9 does not produce any deviation of the beam of light which is simply darkened, with the low intensity of the light source 6 precluding an effect of diffraction at the periphery of the foreign body 9. In this manner, the captor 3 is not excited by the presence of soil which does not deform the surface of the glass and which therefore should not constitute a cause for rejection of the glass.

The possibility of selection offered by the present process, designated the "mixed field" process makes it possible to discriminate between flaws of the glass and soil or deposits which in themselves are not flaws of the material.

It should also be noted that the sensitivity of the system is an inverse function of the distance (x) of the light source 6 from the optical axis 00', as the deviation caused by a flaw and necessary to form an image of it, will also be smaller. However, in order to maintain the captor at the border of the fringe of the blurred image of the light source, the light source must not be placed on the axis 00' itself. As the light source is moved closer to the axis 00' the photosensitive system will be able to detect the slightest deviation of the light rays caused by a very small deformation of the glass.

Figure 3A:
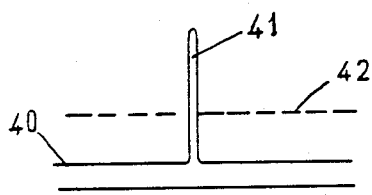
FIGS. 3A and 3B are schematic representations of the configuration of the signal that may be observed on an oscilloscope screen in the case of a flaw and of dirt.
Figure 3B:
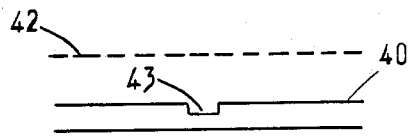
Figure 4:
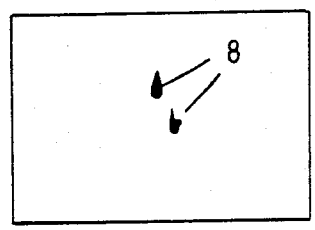
FIG. 4 is a view of a numbered image of flaws produced on a video screen.

Such a result is illustrated by FIGS. 3A and 3B, which represent the effect obtained on an oscilloscope by the appearance of a flaw (FIG. 3A) and of soil (FIG. 3B). The materialization of the limit 40 of the image of the light source 6 is designated the "light threshold". It is seen that a flaw (FIG. 3A) is translated by an intense luminous peak 41, attaining or surpassing the "flaw threshold" 42. In contrast, a spot of dirt (FIG. 2B) appears as a loss of luminosity 43, lower than the normal light threshold 40, which lower light intensity produces an emission of a different flaw signal by the captor. The two different signals makes possible a selection in a comparator stage. By employing a numerical system, the image of the flaws 8 will appear on a video screen in the exact shape and according to the coordinates of the flaws, as a luminous spot on a drak background, while spots of soil do not appear at all (FIG. 4).

Figure 5:
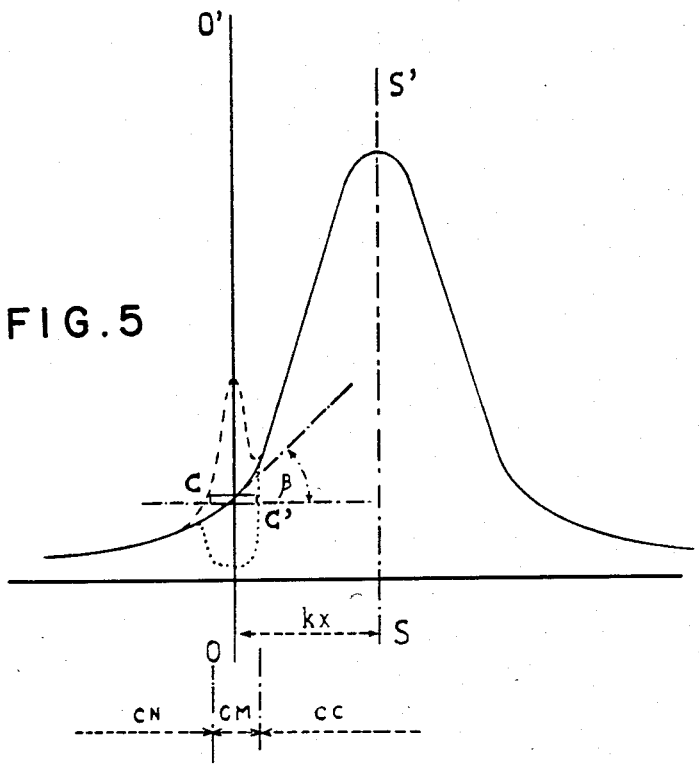
FIG. 5 is a diagram of the luminous intensity at the level of the captor.

FIG. 5 illustrates graphically the luminous intensity received by a segment CC' of the photosensitive captor 3. The segment CC' comprises a transverse section of a grid of photodiodes centered on the optical axis 00' of the convergent system. The image of the light source 6 exhibits its maximum intensity on an axis SS' parallel to optical axis 00' at a distance from the optical axis by the value (kx) defined hereinabove. In the case of normal transmission through the plane formed by the sheet of glass without a flaw, the captor located on the segment CC' receives only a slight amount of light, the value of (y) in this location being considered the "light threshold". This condition is obtained when the half of the segment CC' centered on 00' is less than (kx).

In contrast, if there is a deformation of any kind on the surface of the sheet of glass 1, the light rays will be deflected by refraction in different directions. This deflection causes in the course of the displacement of the sheet of glass at least a part of said rays to penetrate the optical system forming an image at this instant on the axis 00' of the optical system with an intensity higher than the previously registered light threshold (dashed lines in FIG. 5). If this intensity attains or exceeds the "flaw threshold" corresponding to the luminous intensity necessary to cause the emission by one or several photodiodes of a signal, the signal following processing in a comparator, is used by a decision computer to determine the zone affected by the flaw under consideration.

Inversely, in the case of the presence of a spot of dirt present on the surface of the glass which dirt does not cause any deformation of the material, an obscuration of the luminous intensity is observed when the spot in its course of displacement reaches the optical axis 00′. As received by the captor, the intensity is less than the normal light threshold (dotted line in FIG. 5). The darkening produced in this manner causes the emission of a signal which, digitalized, will be different from the signal emitted during the passage of a flaw, resulting in the selection desired.

The foregoing also demonstrates the fact that the sensitivity of the system is an inverse function of the distance (x) of the light source from the axis 00′, or an inverse function fo the distance (kx) of the grid of photodiodes from the axis of the image of the light source received in the plane of the photodiodes. In this way, it is possible to capture even the smallest flaws in spite of the very weak deviation that they cause. This distance should therefore be as small as possible, without, however, placing the light source 6 on the optical axis 00′, so that the captor will not receive directly the image of the light source itself. The limit of this distance value is obtained when the optical amplification, defined by the function $Go = dAo/dx$, attains the value G limiting optical conduction (A being the amplitude of the photodiode and G being expressed in mm volt per millimeter).

FIG. 5 illustrates the three characteristic zones of the observation of flaws: the zone of the bright field (CC) generally used for the simultaneous detection of flaws and soil, the zone of the dark field (CN) used principally in micrography and the so-called zone of the "mixed field" (CM). The "mixed field" (CM) exhibits the above-defined characteristics and at the "mixed field" (CM) is placed the detector 3 at the exact point where the optical amplification represented by the angle $\beta$ is at its optimum value.

Figure 6:
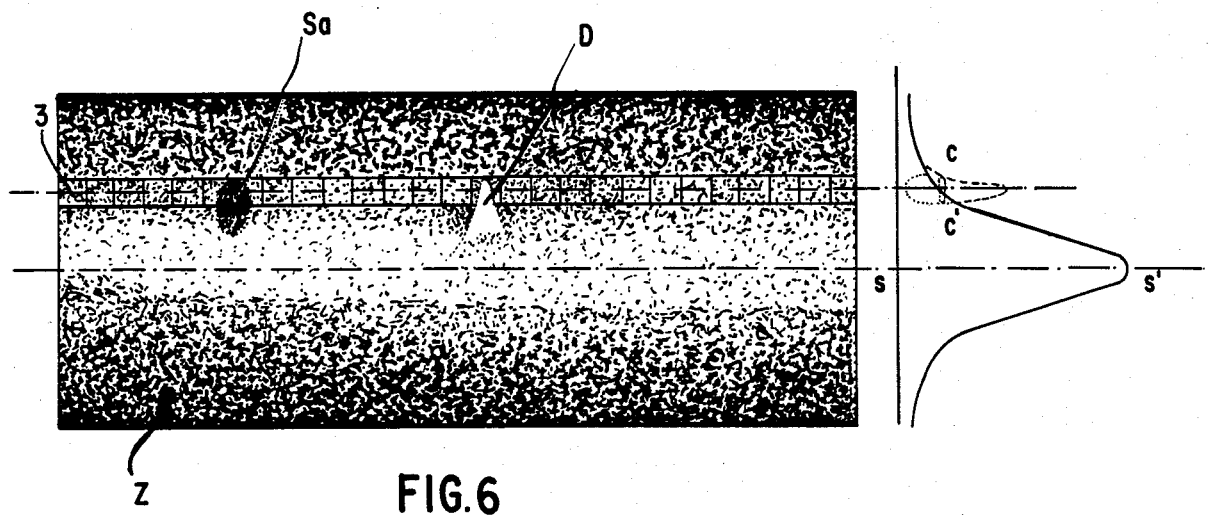
FIG. 6 is a pictorial representation of the diagram of FIG. 5.

FIG. 6 is an analog representation of the zones diagrammatically shown in FIG. 5 (reproduced at the extreme right of the figure). The light zone Z corresponds to the curve of the luminosity of images received by the captor. The photodiode assembly 3 is arranged at the limits of the image of the source of light. It should be noted that an observer placed in the same location as that of the grid 3 of the photodiodes would observe a flaw exactly as shown in FIG. 6, i.e., as a luminous peak D emerging from a bright-dark zone while a spot of soil would appear as a darker spot (Sa) with the exact outline of the spot of dirt.

Figure 7A:
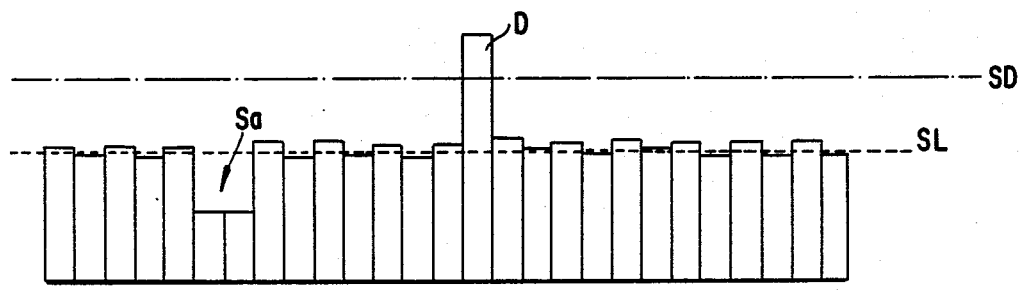
FIGS. 7A and 7B are representations of integrated video signals and of the numerical information emitted by the captor.
Figure 7B:
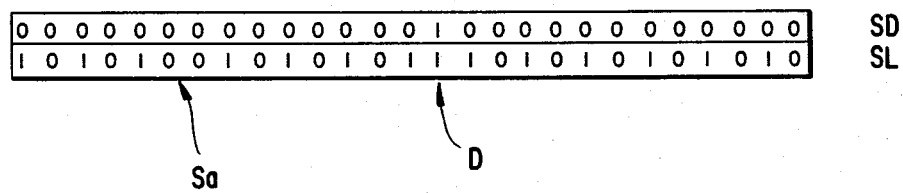

The observation of flaws may also be interpreted in the digital form after information processing. With reference to FIG. 7A, an integrated video image includes a light threshold SL which may be seen at the level where all of the signals emitted by the photodiode in the absence of a flaw are located and a flaw threshold SD attained or exceeded by a signal of the detection of a flaw. Digitalization is effected as indicated in FIG. 7B.

Figure 8:
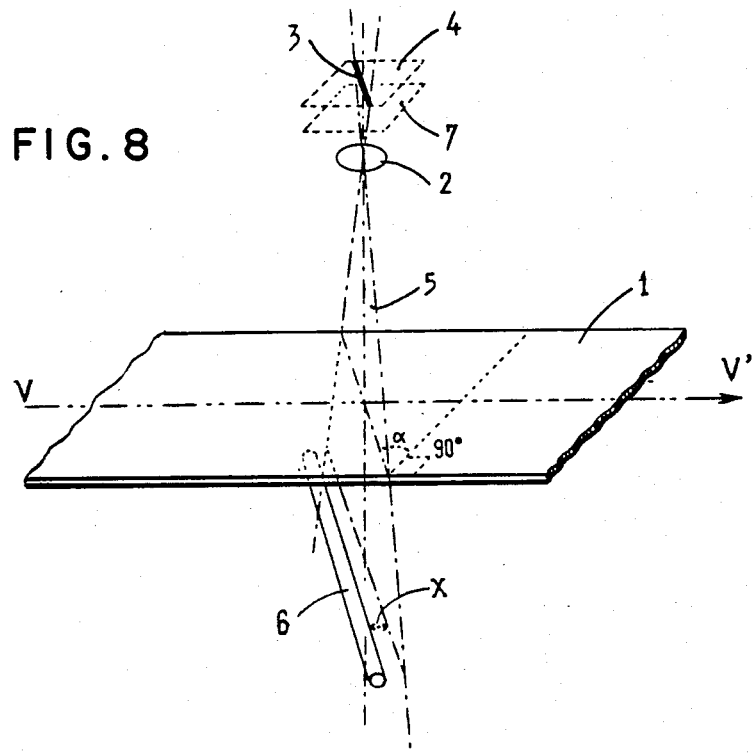
FIG. 8 is a schematic view of the general layout of a device for the application of the process according to the present invention in the case of the inspection of a continuous sheet of glass.

With reference to FIG. 8, a device for the application of the present process includes a sheet of glass 1 to be inspected which sheet travels in the direction of the arrow in a plane located outside the focus of the convergent optical system 2. The optical axis 00′ of the optical system 2 is orthogonal to the plane of the glass in the vertical geometric plane passing through the median VV′ of the sheet. A grid of photodiodes 3 is located at the intersection of a plane 4 of the actual clear image of the sheet of glass (together with all of which it supports) produced by the optical system 2 and of a plane 5 orthogonal to the sheet of glass 1 and containing the optical axis 00′. The length of the captor 3 is at least equal to the length of the actual image of the zone of the sheet of glass 1 illuminated in a mixed field by the source of light 6 located under the sheet 1.

According to the present invention, the light source 6, which may consist for example of a fluorescent tube placed under the glass, is parallel both to the glass and to the vertical plane 5 which contains the grid of photodiodes 3 and the optical axis 00′. The light source 6 is arranged at a distance (x) from this palne 5, so that the image of the light source is found clearly in an image plane 7 distinct from the plane 4 of the photodiodes. Therefore, the light source appears blurred at the plane 4 of the photodiodes, and at a distance (kx) from the axis 00′. In this way, the mixed field is defined at the limits of the plane of the photodiodes.

The value of (x), which is determined experimentally, must be determined in a highly accurate manner. It may, however, vary as a function of the thickness of the sheet of glass, the tint of the glass, and/or the refraction index of the glass. It may also vary during the inspection of the same sheet of glass as a result of the possible movements of the base of the apparatus due to mechanical or thermal causes.

The precision required of the distance value of (x) at any given point for the linear source of light is more critical than the accuracy of the parallelism of the light source 6 and the captor 3.

Figure 9:
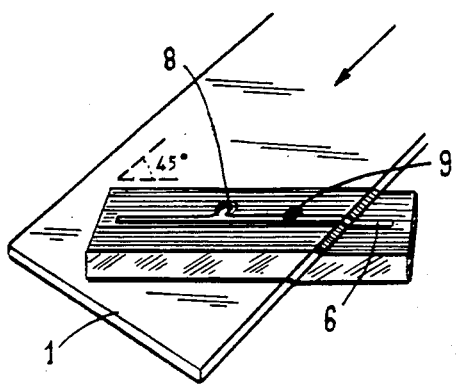
FIG. 9 is a schematic view of the image seen by an observer of a point defect on the surface of the glass according to the process of the present invention.
Figure 10:
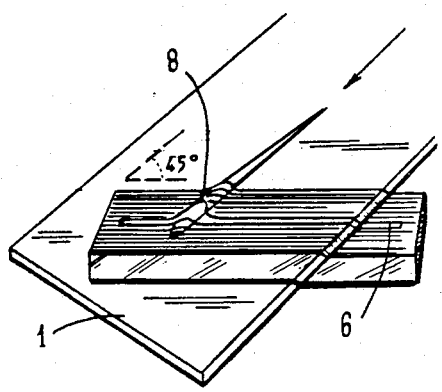
FIG. 10 is a schematic view of the image seen by the observer of a longitudinal defect of the glass surface according to the same process of the present invention.

It has been found further that to render even more apparent the flaws and to increase the contrast with respect to the light threshold, it may be desirable to orient the light source 6 at an angle $\alpha$ (generally 45°) in relation to the direction of displacement VV′ of the glass, with the light source 6 remaining parallel to the sheet being inspected. The result obtained is shown in FIG. 9 for the case of a flaw consisting of a bubble. The contrast effect produced by the angular orientation of the light source with respect to the longitudinal direction of the sheet being inspected is even more apparent in the case of drops, which are extended flaws appearing very slightly on the surface. FIG. 10 illustrates what would appear to an observer during the passage of a drop. The drop causes a more luminous image of the light source being extended and being illuminated at the level of the flaw, thereby rendering the flaw easily detectable in the captor.

With reference to FIG. 11, different results are obtained for the level of the light threshold during a very small displacement of the grid of photodiodes with respect to the image of the light source 6 when the parallelism between the captor 3 and the source 6 is maintained (FIGS. 11a to 11f) and when it is altered (FIGS. 11g to 11l). In both cases a reduction in the value (kx) at any given point of the captor 3 considerably increases the intensity of the light threshold at the corresponding point of the image. And inversely, an increase in the value (kx) decreases the light intensity. Accordingly, it is preferred that the value (x) or consequently the value of (kx) be maintained constant and accurate. The present invention therefore provides an automatic device for aligning the grid of photodiodes 3 to keep the grid constantly parallel to the light source 6, which in this embodiment is stationary and produces a constant distance (kx) from the center of the axis 00′ to the blurred image produced from the light source. In this way, the optical amplification remains optimal and constant.

For this purpose (FIG. 12), the assembly of the photodiodes is mounted on a horizontal plate 9 integral with toothed sectors 10 diametrically opposed to the optical center OO' of the grid 3. The toothed circular sectors 10 each engage one of a pair of endless screws 11 which are parallel to each other and perpendicular to a median diameter of the circular sectors 10.

Each of the endless screws 11 is actuated in rotation by any suitable reversible mechanical connection, for example another endless screw. The additional endless screws are connected to a stepping motor 12 controlled by a computer, the function of which shall be described hereinafter. The endless screws may be placed into a rotating movement independently of each other, in the same direction and at the same velocity. The result of this movement is a displacement of the grid of photodiodes 3 parallel to each other. Each of the stepping motors 12 may further impart a rotating movement to each of the endless screws 11 in different directions and at different velocities. The result of this movement is to effect the displacement of the grid 3 by a predetermined angle.

Each of these movements, allowing the necessary precision by virtue of the reduction obtained, constantly keeps the grid of photodiodes 3 in the plane 5 parallel to the light source 6 (FIG. 8) and at the distance (kx), predetermined experimentally by manually controlling the displacement of the plate 9 until maximum optical amplification is attained. The point of optimal amplification may be obtained by causing the beam of light to traverse a flaw of any nature affecting a sheet of glass of any type, with the position of the captor 3 determined in this manner being entered into a memory so that this position may be maintained automatically.

Figure 13:
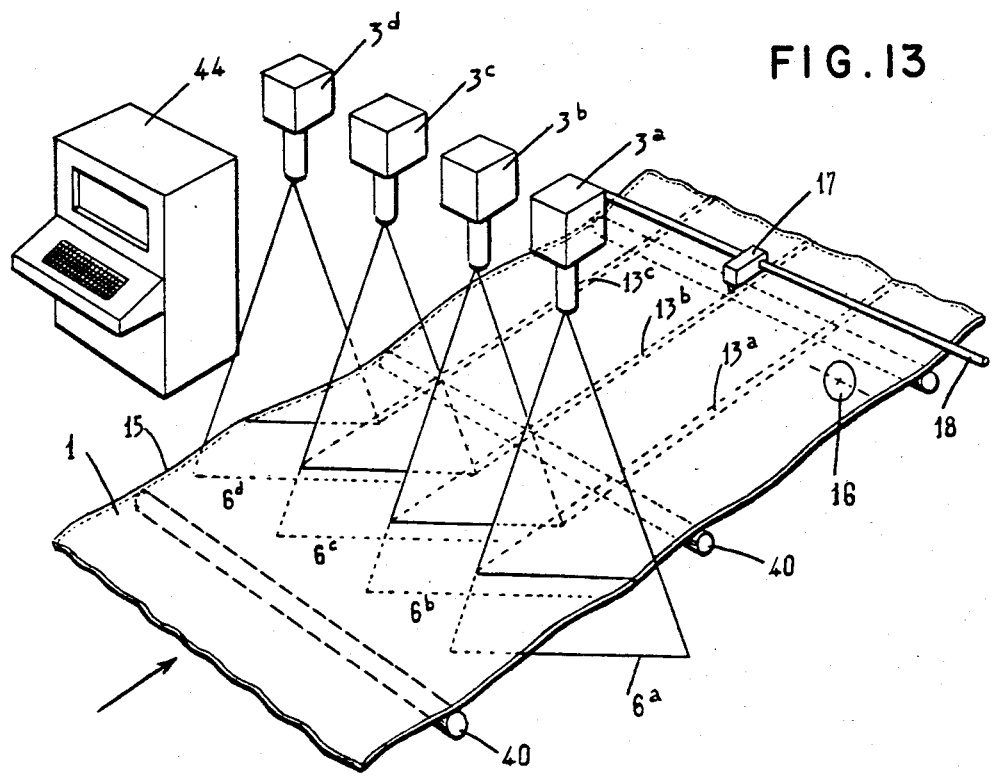
FIG. 13 is a schematic view of a device for applying the process of the invention in the case of the inspection of a strip of glass in the course of manufacture.

An apparatus set up in this manner is effective for the surveillance of continuous sheets of glass in the course of their manufacture, at the outlet of the tin bath which constitutes the characteristic of the production process technically designated the "float glass" process. In this manner, the inspection is performed by covering the entire width of the sheet by as many linear sources of light as necessary (FIG. 13). Each of these linear sources or light illuminating devices 6a, 6b, 6c, 6d are placed at an angle α with respect to the direction of displacement of the sheet of glass to be inspected. Independent of the advantage afforded by this oblique position in the detection of flaws described above, the angular orientation of the illuminating devices makes it possible to lay out the oblique illumination over the entire width of the band in the space left free between two rolls 40 supporting the glass band without the rolls 40 interfering with the operation of the apparatus. The fields illuminated by each of these sources of light are partially overlapping at 13a, 13b, 13c in the direction of the width of the sheet of glass 1. Accordingly, there will be no gap in the transverse zone to be inspected.

As indicated hereinbelow, the electronic assembly for the analysis of the signals emitted by the photodiodes makes it possible to enter the signals received in each of the zones covered by the first grid excited, 3a for example, in the direction of the passage of the sheet 1, so as to inhibit a second signal generated by the same flaw in the same zone at the level of the second gird 3b.

Furthermore, as a result of the length of the sheet of glass drawn according to the aforementioned production process, and of the residual plasticity of the glass during cooling, it has been found that the edges 14 and 15 of the strip are not perfectly rectangular, even though they are maintained in a horizontal plane. These edges 14, 15 represent what the glass makers call the lateral "distortion", appearing in FIG. 13. Thus, to prevent the generation of signals by lateral alignment and flatness defects at the level of the edges 14, 15 in the end captors 3a and 3d an electronic end masking program is preferably introduced in the computer to render the photodiodes corresponding to these edge zones blind. The edge zones are ordinarily subsequently systematically cut off to be remelted.

Furthermore, a tachometer 16 of any type, such as a wheel entrained by the surface of the glass 1, makes it possible to determine the velocity of passage and to derive from the velocity the longitudinal abcissa or location of a flaw detected by any of the grids of photodiodes. The knowledge of the number of the photodiode or diodes yields the transverse ordinates of the corresponding flaw. All of this information is entered in the memory to ensure the actuation of an automatic marking system 17, when the flaw in reference reaches an active zone of the marking system. The marking system 17 may consist, as an example only, of a device equipped with a liquid atomizer or more simply of a grease marker used by glass makers, capable of being displaced along a transverse rail 18, so as to be at the exact level of the transverse ordinate of the flaw at the precise instant when the flaw appears under the marking system. The marking system 17 is then actuated as a function of the longitudinal abcissa information previously entered in the memory (possibly together with an assembly of markers in juxtaposition, sufficiently numerous to cover the width of the sheet in a quasi-continuous manner). The actuation of the marker system may be effected in a fashion similar to piano keys.

The apparatus according to the present invention may be further completed by the continuous projection of compressed air at each light illuminating device to ensure constant dusting of the light sources. This particular device is not illustrated in the drawing figures.

Figure 15:
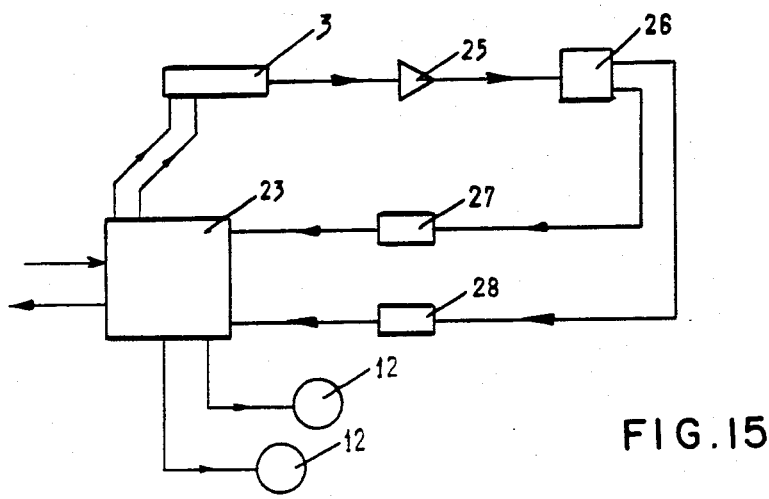
FIG. 15 is a schematic view in a block diagram of the captor itself.
Figure 14:
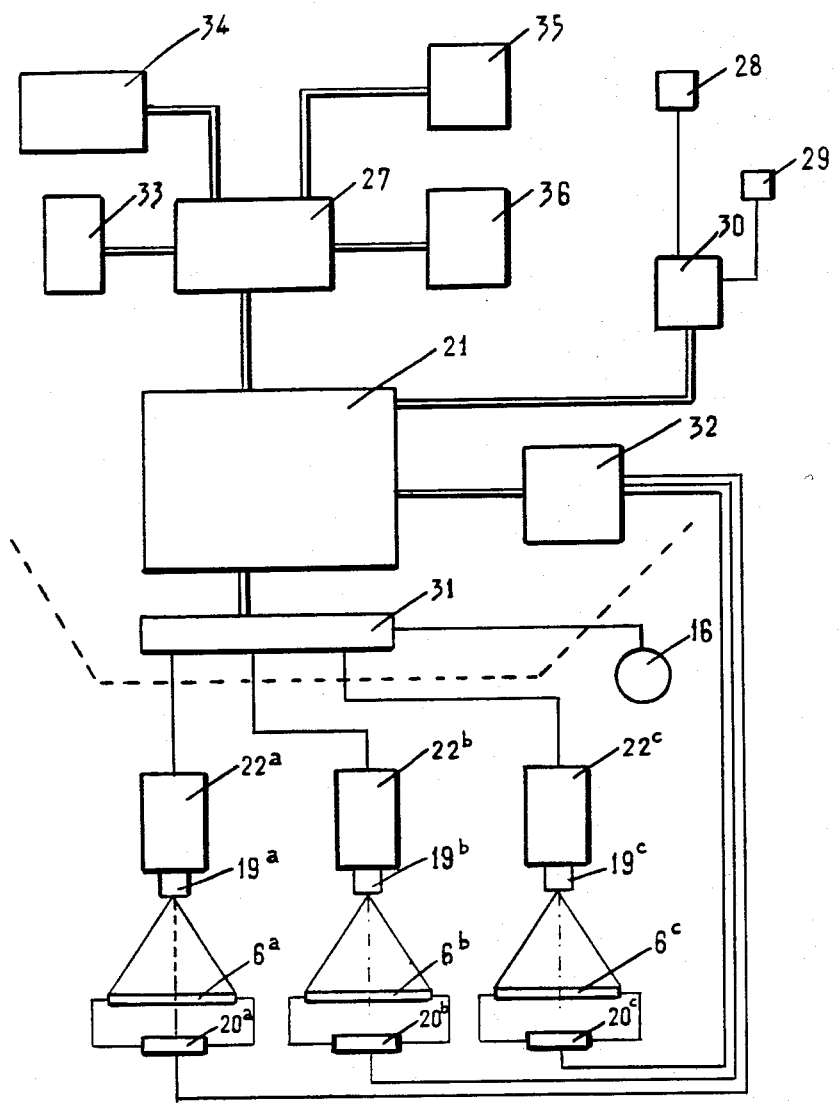
FIG. 14 is a schematic view in a block diagram of the electronic assembly for the analysis of the signals emitted by the captor for rendering the decisions necessary both for the automatic maintenance of optimal optical conditions for inspection within the process of the present invention and to account for a flaw detected with the exception of dirt in keeping with the instructions entered in the memory, and consequently for issuing corresponding orders both to control devices for the light source and for the position of the light source in relation to the captor and to peripheral elements to indicate the flaw detected or reject the portion of the glass affected.

The detection of flaws is effected, as described hereinabove, by the grid or grids of photodiodes 3 (sufficient in number to cover the width of the sheet to be inspected) The reception of the signals emitted in this manner and their analysis, together with the interpretation and transmission of instructions derived from the signals is effected by electronic assemblies through a specially designed and organized function computer (FIGS. 14 and 15).

With reference to FIG. 14, the linear sources of illumination 6 are placed under the sheet of glass to be inspected, at a distance as large as permitted by the normal configuration of a glass making machine of the above-described process. The light sources are arranged in a plane parallel to the sheet and in a manner such that their respective illuminating zones overlap in succession (FIG. 13). The sheet of glass is exposed to observation by cameras 19, each of which contains the optics 2 and the grid of photodiodes 3 mounted on a plate 9. Each camera is automatically aligned by individual stepping motors 12. Each of the light sources 6, consisting of a fluorescent tube, is supplied by a converter 20 providing an adequate voltage at a frequency of 25 KHz to obtain substantially perfect constancy of luminosity by virtue of the inertia of the luminescence of this system. The luminescence itself is controlled by a common computer 21, designated the decision computer, which is receiving information supplied by the captor elements 22a, 22b and 22c associated with each optical camera 19. Each of these captors 22 itself includes a computer 23 (FIG. 15) which controls the grid of photodiodes assigned to the respective computer 23 to ensure a scanning frequency commensurate with a timing period corresponding to the frequency necessary to assure the continuous observation of the entire surface of the glass as a function of its velocity detected by the tachometer 16.

For example, for a velocity of advance of the glass of 400 mm/s and the zone observed by the photodiodes being 0.35 mm, the frequency of scanning required is 1.14 KHz, with the timing frequency from diode to diode in this instance being 0.6 MHz for a grid of 512 photodiodes. These functions are actuated by the computer 23 attached to the captor. The computer 23 is capable of issuing instructions to the stepping motors 12 for the automatic maintenance of the grid of photodiodes 3 in the zone for optimum optical amplification.

The signal emitted by the photodiode or diodes of the rays deflected by a flaw appearing in the surface of the glass is fed to an amplifier 25. The amplified flaw signal is fed to a comparator 26 which further receives information concerning both the light threshold corresponding to the level of illumination existent in the absence of a flaw, and the flaw threshold concerning the illumination level that must be considered an aberration, to detect a flaw. The signals received by the comparator 26 and originating in the grid of photodiodes are compared with each of these thresholds to yield the information emitted by the comparator 26 and addressed individually to buffer storage memories 37 and 38. The buffer storage memories store separately the light and flaw information to be integrated by the captor computer 23. The captor computer 23 is then able to transmit information to the decision computer 21 (FIG. 14), which, as a function of the criteria supplied by a dialogue computer 27, issues instructions to the marking systems 17, or to automatic cutting peripherals 29 through a universal interface 30.

According to FIG. 14, the block diagram of the assembly of the apparatus is comprised essentially of elements to acquire the data, from either side of the sheet 1, formulated by the linear emitters of luminous flux or light sources 6 supplied at 25 KHz by the converters 20 and the optical cells or cameras 19. The optical cells 19 focus the image of flaws on the grid of photodiodes 3 contained in the captors 22, which themselves comprise (FIG. 15) the captor computer 23 which both controls the scanning frequency of the grids 3 and receives the signals emitted by grids after comparison of these signals in the comparator 26 with the light threshold and the flaw threshold. The captor computer 23 transmits the information created in this manner to the decision computer 21 through the station 31, designated the emission-reception station, which also receives the information from the tachometer 16 and provides filtering, thereby making possible operation in a parasitic medium.

The decision computer 21 further receives from the dialogue computer 27 the data that are considered the base criteria. In this way, the decision computer may transmit instructions when such criteria are or are not attained through the power amplifier 32 and in certain cases to the stepping motors 12 for controlling the position of the grids of photodiodes in the zone of optimum optical amplification of the mixed field. Further, the decision computer 21 may transmit instructions to the converters 20 of variable luminosity to control the luminous intensity as a function of instantaneous requirements and finally to control, in communication with the captor computer 23, the frequency of scanning by the grids of photodiodes as a function of the passage velocity of the glass, for which information is supplied to the decision computer 21 from the tachometer 16.

Furthermore, as mentioned hereinabove, the decision computer 21 is controlling, as a function of the existence of a flaw and through the interface 30, the glass marking devices 17 or the automatic cutting devices 29, the activation whereof is the purpose of the apparatus of the present invention.

In order to ensure the dialogue with the decision computer 21, the dialogue computer 27 is coupled with command peripherals, such as a keyboard 33, or with control peripherals, such as a screen 34 and a printer 35, together with a mass memory, such as magnetic disks 36, or any other device that may be necessary. The assembly of the emission-reception station 31, the computer 21, the amplifier 32, the interface 30 and the dialogue computer 27, together with the peripheals, are contained in a cabinet excluding the data acquisition elements 6, 20, 19 and 22. It is recommended in order to ensure perfect accuracy of the results obtained, to effect 10,000 measurements of the signal furnished by each photodiode, with the order finally transmitted being the result of the analysis of the average of the measurements. This arrangement makes it possible to attain an accuracy of 1/100 millivolts in the signal of the photodiodes received.

An apparatus of this type is particularly adapted for the inspection of glass passing continuously from the outlet of the manufacturing station described hereinabove. However, the process is capable of being used for the inspection of glass already cut, such as for example sheets of glass intended for the manufacture of laminated or tempered windshields.

If the detection of flaws is effected prior to the application of multiple layers or of tempering, it is desirable to permit detection of flaws of the glass in the material itself and also dirt which may soil its surface in spite of prior washing of the precut sheets. It is necessary prior to tempering or the application of the layers that the glass does not carry any trace of dirt during the assembly of multiple layers or during tempering, as such dirt would be irreparably fixed on it.

In this particular case and with reference to FIG. 16, an additional illuminating device of higher intensity is included with the illuminating device 6 described hereinabove to make it possible to detect even the smallest flaws affecting the surface of the glass. The additional source of light is removed from the optical axis not to the borders of the bright field and the mixed field, as is the light source 6 (according to FIG. 5), but to the extreme limits of the mixed field and the black field (according to the same figure). In this way, it is feasible, as indicated hereinabove, to detect foreign bodies deposited on the surface of the glass by virtue of the diffraction effect created at the periphery of the foreign bodies. Another such illuminating device 37 is positioned to illuminate the lower part of a glass plate 38 cut in the shape of a windshield, in order to detect any dirt adhering to its surface. Still another illuminating device 39 is placed at the upper part to complete this inspection. The distances x' and x" of these light sources from the optical axis is such that the above-specified conditions are satisfied.

In the case where the illumination device 37 is removed from the optical axis to the point where high power is needed, such high power illumination may be obtained by halogen tubes.

According to FIG. 17, the tachometer 16, which in this case is linked with the rollers carrying the windshield 38, serves to digitize the dimensions of the windshield 38 and to create along this piece a neutral zone which is not being analyzed. The edge of the windshield 38 is systematically interpreted as a defect. This is apparent in FIG. 18, wherein the spectroscopic curve of a windshield is represented. With reference to FIG. 18, the edges are simulating the flaws (a) and (b), an impurity or a real flaw being located between these limits, at (d) for example. The inlet and outlet positions of the windshield 38 are thus determined with precision by the computer, together with its exact width. In this way, it is possible to determine, again with precision, the coordinates of a flaw that may be detected.

The present invention makes it feasible to detect all of the defects affecting the surface of a flat sheet of glass, whether such sheets are travelling continuously or in separate sections. In addition, the present invention permits detection of either flaws only of the material with the exclusion of spots of soil deposited on its surface, or including the latter when necessary. The process according to the present invention is also capable of being applied to the detection of flaws of any transparent surface other than glass.

The principles, preferred embodiments and mode of operation of the present invention have been described in the foregoing specification. However, the invention which is intended to be protected is not to be construed as limited to the particular embodiments disclosed. The embodiments are to be regarded as illustrative rather than restrictive. Variations and changes may be made by others without departing from the spirit of the present invention. Accordingly, it is expressly intended that all such variations and changes which fall within the spirit and scope of the present invention as defined in the claims be embraced thereby.

What is claimed is:

1. A method for permitting the examination of transparent sheets for the purpose of detecting flaws in the sheets and for discriminating between the flaws and opaque foreign bodies deposited on the transparent sheet comprising:

lighting the width of one of the sides of the transparent sheet by means of a source of light parallel to each sheet having a small longitudinal opening and being of weak intensity for producing diffused light;

forming a clear, real image of the light source in an imaginary plane located slightly spaced from a photodetector device with a convergent optical system located on the other side of the transparent sheet being observed within an access perpendicular to the plane of the sheet;

positioning the photodetector device in a plane parallel to the sheet and the light source such that an optical axis of the photodetector device is at a distance (x) from the light source so that the detector device receives, in a constant manner, a fringe of a fuzzy image in a first plane of the real image of said light source, said real image being in said imaginary plane located slightly spaced from the photodetector device;

adjusting the intensity of the light source to be weak enough so that a threshold amount of constant light received by the photodetector, on which is formed the fringe of the fuzzy real image of the light source, will always remain below an excitation threshold of an analyzing system which receives and processes signals generated by the photodetector device;

reaching and exceeding said excitation threshold at the time of a passing of a flaw of the sheet under examination which flaw causes the deviation of a light beam of the light source by refraction, thereby forming a bright real image of said flaw on the photodetector device, in addition to the fuzzy image which is constantly received by the photodetector, which bright real image causes the generation of a signal which is recorded and processed by the analyzing system, said fuzzy image received by the photodetector at a predetermined distance (kx) from the optical axis of the photodetector; and causing a real image of less intensity than the constant light received by the photodetector device upon the passing of an opaque body deposited on the transparent sheet under examination which real image of less intensity is less than the threshold amount of light and generates a signal, different from the signal generated by the bright real image which different signal is recorded and processed by the analyzing system whereby discrimination between the flaws and the opaque body is assured by a single photodetector assembly located at a single location.

2. The method according to claim 1, wherein the optimal position of the light source in relation to the optical axis of the photo detector device is such that at this position the optical gain representated by $Go = -dAo/dx$ is optimized with A being the amplitude of the signal generated by the detector device and (x) being the distance between the light source and the optical axis of the detector device, said position of the detector in relation to the light source being defined as a zone of "mixed field" intermediate between a zone called "bright field" which contains the maximum of lightning and the zone called "black field", such that the diffractive effect caused by the opague bodies which effect occurs in the zone called "black field" is excluded.

3. An apparatus for permitting the examination of transparent sheets for detecting flaws in a sheet and for discriminating between the flaws and opaque foreign bodies deposited on the transparent sheet, comprising means for moving the sheets, a light source located below the transparent sheet to be checked, said light source being thin and linear and arranged at a 45° angle in relation to the direction of movement of the sheet, said light source being parallel to the horizontal plane of said sheet and being parallel to a vertical plane containing an optical axis of a convergent optical system and a linear network of photodiodes which constitute a receiving organ for the light from the light source, said light source being located at a distance (x) relative to the vertical plane such that the linear network is externally tangent to a fringe of a fuzzy real image produced by the optical system in a plane of the network of photodiodes, the lengths and positions of the light source and of the network of photodiodes being such that the fuzzy real image which the optical system produces of the light source in the plane of the network, covers the length of this network whereby sweeping of the whole of the surface of the sheet is accomplished without any moving mechanical element interposed between the light source and the network of photodiodes, adjustment means for maintaining constant both the distance (x) at which the light source is located from the vertical plane containing both the optical axis of convergent optical system and the linear network of photodiodes and the parallelism of the light source with the vertical plane such that the optical gain will always be optimal over the whole length of the linear network in spite of the variations in either the nature of the transparent sheet to be checked or dimensional variations of a chassis of the apparatus, said adjustment means includes a plate for mounting the linear network of photodiodes, said plate being provided with two toothed circular sectors diametrically opposed on each side of the network and a worm screw associated with each of the circular sectors activating the circular sectors either simultaneously or individually at equal or different speeds and in the same direction or in opposite directions, said worm screws being driven by two motors step by step controlled independently from each other in response to the amount of light received by each one of photodiodes, whereby the network can be moved automatically either in a direction parallel to itself or at an angle and the network may be subjected to two simultaneous movements so as to be moved on the resultant of the movement to a desired value (kx), K being the coefficient of reduction of the optical system.

4. An apparatus for permitting the examination of transparent sheets for detecting flaws in a sheet and for discriminating between the flaws and opaque foreign bodies deposited on the transparent sheet, comprising means for moving the sheets, a light source located below the transparent sheet to be checked, said light source being thin and linear and arranged at a 45° angle in relation to the direction of movement of the sheet, said light source being parallel to the horizontal plane of said sheet and being parallel to a vertical plane containing an optical axis of a convergent optical system and a linear network of photodiodes which constitute a light receptor element for the light from the light source, said light source being located at a distance (x) relative to the vertical plane such that the linear network is externally tangent to a fringe of a fuzzy real image produced by the optical system in a plane of the network of photodiodes, said plane also containing a clear, real image of the sheet, the lengths and positions of the light source and of the network of photodiodes being such that the fuzzy real image which the optical system produces of the light source in the plane of the network, covers the length of this network whereby scanning of the whole of the surface of the sheet is accomplished without any moving mechanical element interposed between the light source and the network of photodiodes with a frequency of said scanning determined by computer control.

5. The apparatus according to claim 4, further comprising a plurality of detecting assemblies placed side by side, each assembly including a light source on one side of the transparent sheet and an optical system and a detecting network of photodiodes on an opposite side of the sheet, each assembly being oriented at a 45° angle in relation to the direction of the movement of the transparent sheet, the position of each of the assemblies including at the common limit of adjacent ones of the assemblies an overlapping zone of their light projections in order to avoid any interval between the assemblies.

6. The apparatus according to claim 4, further comprising a tachometer for providing data concerning the speed of movement of the transparent sheet for aiding in the determination of the coordinates of the flaw detected, the number of a photodiode excited by a refraction of a light beam from the light source caused by the flaw providing a lateral coordinate and the tachometer providing the longitudinal coordinate, the data from the tachometer also permitting determination of a sweeping frequency of the networks of photodiodes such that the whole of the surface of the sheet is checked regardless of the speed of movement of the sheet.

7. The apparatus according to claim 6, further comprising a marking device driven by the data of coordinates provided for the location of the flaw on the sheet, said marking device including a carriage movable on a guide spanning the whole width of the sheet, a motor for moving the carriage, said motor having a fast starting and braking arrangement which receives the data of the lateral coordinate determined by the number of the diode excited by the corresponding flaw, the starting of the marking itself being done according to the longitudinal coordinate determined through the data provided by the tachometer, means for memorizing the data at the time of detection of the flaw, the marking device including a solid body able to leave a showing mark on the checked sheet, means for lowering the marking device until said body contacts the surface of the sheet at the location for the marking of the flaw.

8. The apparatus according to claim 4, wherein the light source is arranged in a box having a longitudinal slit for light, the longitudinal slit being subjected to the action of a blower of compressed air for avoiding dusting of the longitudinal slit of the light source.

9. The apparatus according to claim 7, wherein electric signals provided by each of the photodiodes of the detecting network are sent, after being amplified, to a comparator, said comparator also receiving data relating both to a light threshold of the fringe of the fuzzy image and to a fault threshold indicative of illumination level indicative of the refraction of the light beam, a captor computer for individually memorizing and analyzing the data, said captor computer providing results for a transmitter receiver station which also receives data from the tachometer, a decision computer receiving results from the transmitter receiver station, said decision computer providing orders to elements of the apparatus including a power amplifier for adjusting the intensity of the light source in order to maintain constant the light intensity in the linear network, a device for electronic adjustment of the sweeping frequency of the photodiodes in relation to the speed data received by the tachometer, and the marking device for starting the marking in relation to the coordinates of the flaw, said captor computer controlling adjustment means for maintaining constant both the distance (x) of the photodiode network in relation to the image of the light source as well as the parallelism of the network in relation to the light source.

10. The apparatus according to claim 4, further comprising an electronic blanking for automatically blinding the photodiodes corresponding to an image of a predetermined width of each one of the longitudinal edges of the sheet in order to avoid signalling as a flaw either the image of the edge of the strip which edge is not always straight or the marks of driving rollers which marks may appear on the edges.

11. The apparatus according to claim 5, further comprising means for both memorizing signals generated by a first network reached by the sheet in the overlapping zones present between adjacent ones of the several light sources and preventing the excitation of the corresponding diodes of the second network reached in the direction of movement of the sheet corresponding to the same overlapping zone in order to avoid a duplicate signal with the signal already generated by the first network concerning the same zone.

12. The apparatus according to claim 9, wherein transverse edges of an individual sheet are detected as flaws by the network of photodiodes to determine the length of a sheet, whereby, taking into account the data from the tachometer, the exact coordinates of a flaw or foreign body within the checked sheet can be determined.

13. The apparatus according to claim 12 wherein sheets of a predetermined configuration may be inspected under a mixed field illuminating assembly so as to detect any defect or opaque foreign body which may prevent subsequent conditioning of said sheet, the mixed field assembly including two additional illumination devices, one of which is located below the sheet of glass and the other is located above the sheet of glass, the two additional illumination devices being simultaneously parallel to the horizontal plane of the glass to be inspected and to the vertical plane of the optical axis and the array of photodiodes and their respective distances (x') and (x") from said vertical plane such that the two additional illumination devices are at the lower boundary of the mixed field.

14. An apparatus for permitting the examination of transparent sheets for detecting flaws in a sheet and for discriminating between the flaws and opaque foreign bodies deposited on the transparent sheet, comprising means for moving the sheets, a light source located below the transparent sheet to be checked, said light source being thin and linear and arranged at a 45° angle in relation to the direction of movement of the sheet, said light source being parallel to the horizontal plane of said sheet and being parallel to a vertical plane containing an optical axis of a convergent optical system and a linear network of photodiodes which constitute a light receptor element for the light from the light source, said light source being located at a distance of (x) relative to the vertical plane such that the linear network is externally tangent to a fringe of a fuzzy real image produced by the optical system in a plane of the network of photodiodes, the lengths and positions of the light source and of the network of photodiodes being such that the fuzzy real image which the optical system produces of the light source in the plane of the network, covers the length of this network whereby sweeping of the whole of the surface of the sheet is accomplished without any moving mechanical element interposed between the light source and the network of photodiodes, electric signals provided by each of the photodiodes of the detecting network are sent, after being amplified, to a comparator, said comparator also receiving data relating both to a light threshold of the fringe of the fuzzy image and to a fault threshold indicative of illumination level indicative of the refraction of the light beam, a captor computer for individually memorizing and analyzing the data, said captor computer providing results for a transmitter receiving station which also receives data from a tachometer which provides data concerning the speed of movement of the transparent sheet for aiding in the determination of the coordinates of the flaw detected, a decision computer receiving results from the transmitter receiver station, said decision computer providing orders to elements of the apparatus including a power amplifier for adjusting the intensity of the light source in order to maintain constant the light intensity in the linear network, a device for electronic adjustment of the sweeping frequency of the photodiodes in relation to the speed data received by the tachometer, and a marking device which marks the location of any detected flaws in the glass, said captor computer controlling adjustment means for maintaining constant both the distance (x) of the photodiode network in relation to the image of the light source as well as the parallelism of the network in relation to the light source.

* * * * *